US00PP13250P3

(12) United States Plant Patent
Utecht

(10) Patent No.: US PP13,250 P3
(45) Date of Patent: Nov. 19, 2002

(54) GERANIUM PLANT NAMED 'FISROVIO'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/991,633

(22) Filed: Nov. 26, 2001

(65) Prior Publication Data

US 2002/0083502 P1 Jun. 27, 2002

(51) Int. Cl.[7] ..... A01H 5/00

(52) U.S. Cl. ..... Plt./329

(58) Field of Search ..... Plt./329

*Primary Examiner*—Kent L. Bell
(74) *Attorney, Agent, or Firm*—Foley & Lardner

(57) ABSTRACT

A new and distinct cultivar of geranium plant named 'Fisrovio', as described and illustrated, and particularly characterized by the combined features of bright violet-purple flowers with orange-red markings, medium-green, slightly zoned foliage, vigorous growth, and well-branched, uniform, tall plant habit.

1 Drawing Sheet

BOTANICAL CLASSIFICATION

*Pelargonium zonale.*

VARIETY DENOMINATION

'Fisrovio'.

BACKGROUND OF THE INVENTION

The present invention comprises a new and distinct cultivar of geranium, botanically known as *Pelargonium zonale,* and hereinafter referred to by the cultivar name 'Fisrovio'.

'Fisrovio' is a product of a planned breeding program which had the objective of creating new geranium varieties with purple flower color in combination with medium-green foliage and medium to tall plant habit.

'Fisrovio' originated from a hybridization made by the inventor, Angelika Utecht in a controlled breeding program in Galdar, Gran Canaria, Spain, in 1995. The female parent was an unpatented hybrid seedling, no. K92-876-2, having dark pink, single-type flowers, dark-green foliage with zonation, medium sized plant habit, and late flowering.

The male parent of 'Fisrovio' was the unpatented hybrid seedling K93-998-6, which was characterized by purple-pink, semi-double flowers, and medium green, zoned foliage.

'Fisrovio' was selected as one flowering plant within the progeny of the stated cross by Angelika Utecht in 1996 in a controlled environment in Galdar, Gran Canaria, Spain. The first act of asexual reproduction of 'Fisrovio' was accomplished when vegetative cuttings were taken from the initial selection in the fall of 1996 in a controlled environment in Galdar, Gran Canaria, Spain, by, or under the supervision of, Angelika Utecht.

Horticultural examination of plants grown from cuttings of the plant initiated in May 1998 in Hillscheid, Federal Republic of Germany, and continuing thereafter, has demonstrated that the combination of characteristics as herein disclosed for 'Fisrovio' are firmly fixed and are retained through successive generations of asexual reproduction. The new cultivar reproduces true to type.

'Fisrovio' has not been observed under all possible environmental conditions. The phenotype may vary significantly with variations in environment such as temperature, light intensity and day length. The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fisrovio' in combination distinguish this geranium as a new and distinct cultivar:

1. Intense violet-purple flowers with orange-red markings;

2. Floriferous with relatively umbels well above the foliage;

3. Medium green, slightly zoned foliage;

4. Vigorous growth, good branching ability, and tall, round plant habit; and

5. Mid season spring flowering response.

Of the many commercial cultivars known to the present inventor, the most similar in comparison to 'Fisrovio' are the patented varieties 'Fisdino' (U.S. Plant Pat. No. 8,761), and 'Baldesvio' (U.S. Plant Pat. No. 11,676) and 'Fistaneon' (U.S. Plant patent application Ser. No. 09/989,368). In comparison to 'Fisdino', 'Fisrovio' has flowers without red macules on the petals, and better branching characteristics that result in a rounder, more uniform, and more floriferous plant habit. In comparison to 'Baldesvio', 'Fisrovio' has a somehat less intense flower color, flowers with fewer petals, longer and mainly green peduncles, while those of 'Baldesvio' are reddish in color and shorter.

In comparison to 'Fistaneon', 'Fisrovio' has a somewhat less intense flower color, lighter green foliage, larger leaves and plant habit is somewhat taller.

BRIEF DESCRIPTION OF THE DRAWING

The accompanying photographic drawing shows typical flower and foliage characteristics of 'Fisrovio' with colors being as true as possible with an illustration of this type. The drawing shows a flowering pot plant in a 14 cm container.

DETAILED BOTANICAL DESCRIPTION

In the following description color references are made to The Royal Horticultural Society Colour Chart (R.H.S.). The color values were determined indoors from plants developed in a greenhouse in May 2001 in Hillscheid, Germany. The measurements were taken in Langley, British Columbia, Canada in early July, 2001, 18 weeks after planting of rooted cuttings. The plants were growing in 8 inch containers and had not been pinched.

Inflorescence:
- *Type*.—Umbel.
- *Shape*.—Semi-spherical.
- *Average diameter*.—121 mm.
- *Average depth*.—68 mm.
- *Peduncle length*.—25 mm.
- *Peduncle color*.—Light green, RHS 143 B.
- *Pedicel, length*.—28 mm.
- *Pedicel color*.—Base green, RHS 144 B, middle part brownish RHS 179 A, upper end, RHS 184 A.
- *Number of flowers per umbel*.—About 25–30.

Corolla:
- *Average diameter*.—50.6 mm.
- *Form*.—Semi-double.
- *Shape*.—Slightly zygomorph, with a gap between upper and lower petals, weakly cup-shaped.
- *Number of petals*.—7.8.
- *Petaloids, number*.—0–2, narrow, color upper part RHS 67 A (like petals), lower part 155 D (Both surfaces).
- *Shape of petals*.—Narrow-obovate to obovate, attenuate base, upper end is truncate or rounded, margin is usually entire and somewhat wavy.
- *Size of petals*.—Upper petals 29–30 mm long, 18–20 mm wide; lower petals 24–25 mm long, 20–22 mm wide.
- *Color* (*general tonality form a distance of three meters*).—Bright purple with orange markings.
- *Color of upper petals*.—Main part between RHS 66 B and 67 A.
- *Markings of upper petals*.—Lower part (almost half the length of the petal) salmon-orange RHS 43 B, furthermore, there are dull-red veins, RHS 53 C.
- *Color of lower petals*.—Between RHS 66 B and 67 A.
- *Markings of lower petals*.—None.
- *Color of lower surface of petals*.—Mainly RHS 67 B, near the base of upper petals RHS 47 B.
- *Color of sepals*.—Outer surface light green, RHS 143 B, at the base brownish RHS 181 A; inner surface light green, RHS 143 C, near the base RHS 179 A.
- *Number of sepals*.—5.
- *Shape of sepals*.—Linear to lanceolate, acute tip, truncate base, surface with weak, very short pubescence, margin entire.
- *Size of sepals*.—9–11 mm long, 4 mm wide for the largest upper sepal, 2–3 mm in width for the other sepals.

Bud (just before petals unfold):
- *Shape*.—Elliptical.
- *Color* (*sepals*).—Green, RHS 143 A, occasionally weak brownish spot at the base, RHS 179 B.
- *Color* (*petals*).—Purple-pink RHS 67 A.
- *Length*.—20 mm, width 13 mm.

Reproductive organs:
- *Androecium*.—5–7 fertile anthers, filaments, whitish, RHS 155 A, plenty pollen, orange-yellow, RHS 30 A.
- *Gynoecium*.—One pistil, dark red style and stigma, color RHS 53 B, 5 to 6-lobed stigma.
- *Fertility/seed set*.—No seed set observed.

Spring flowering response period: In Hillscheid, Germany, in 2000, plants had on average 1.2 flowers opened 8 weeks after planting of rooted cuttings.

Outdoor flower production: Continuously and rich flowering, the flower count in 2000 in Hillscheid, Germany, indicated about 3.2 inflorescences per plant in mid May.

Durability: Good stability of flower color, but somewhat susceptible to being scorched by intense sun light, relatively good rain resistance.

Lastingness of the individual flower: About 9 days at 18° C., about 18 days for the umbel.

Pest/disease resistance/susceptibility: No observations to date.

Fragrance: None.

PLANT

Foliage:
- *Shape*.—Kidney-shaped, with open to wide open, and cordate-shaped base, weak lobes.
- *Margin*.—Bicrenated, slightly wavy.
- *Texture*.—Upper surface smooth, velvety.
- *Size of leaf*.—95 mm wide, 57 mm long.
- *Color of upper surface*.—Medium green, approximately RHS 137 B to RHS 137 C.
- *Color of zonation*.—Brown, about RHS 166 A, relatively weak.
- *Color of lower surface*.—RHS 137 D.
- *Petioles*.—50–65 mm long, 2–3 mm diameter, light green in color, approximately RHS 143 B.

General appearance and form:
- *Stem color*.—Light green, RHS 143 B.
- *Internode length*.—10–25 mm.
- *Branching pattern*.—8.0 branches.
- *Size of plants*.—Height of the foliage canopy 32.6 cm, as measured from the top of the soil/base of the main stem to the upper surface of the foliage canopy without inflorescences, width 58.4 cm.

I claim:

1. A new and distinct cultivar of geranium plant named 'Fisrovio', as described and illustrated herein.

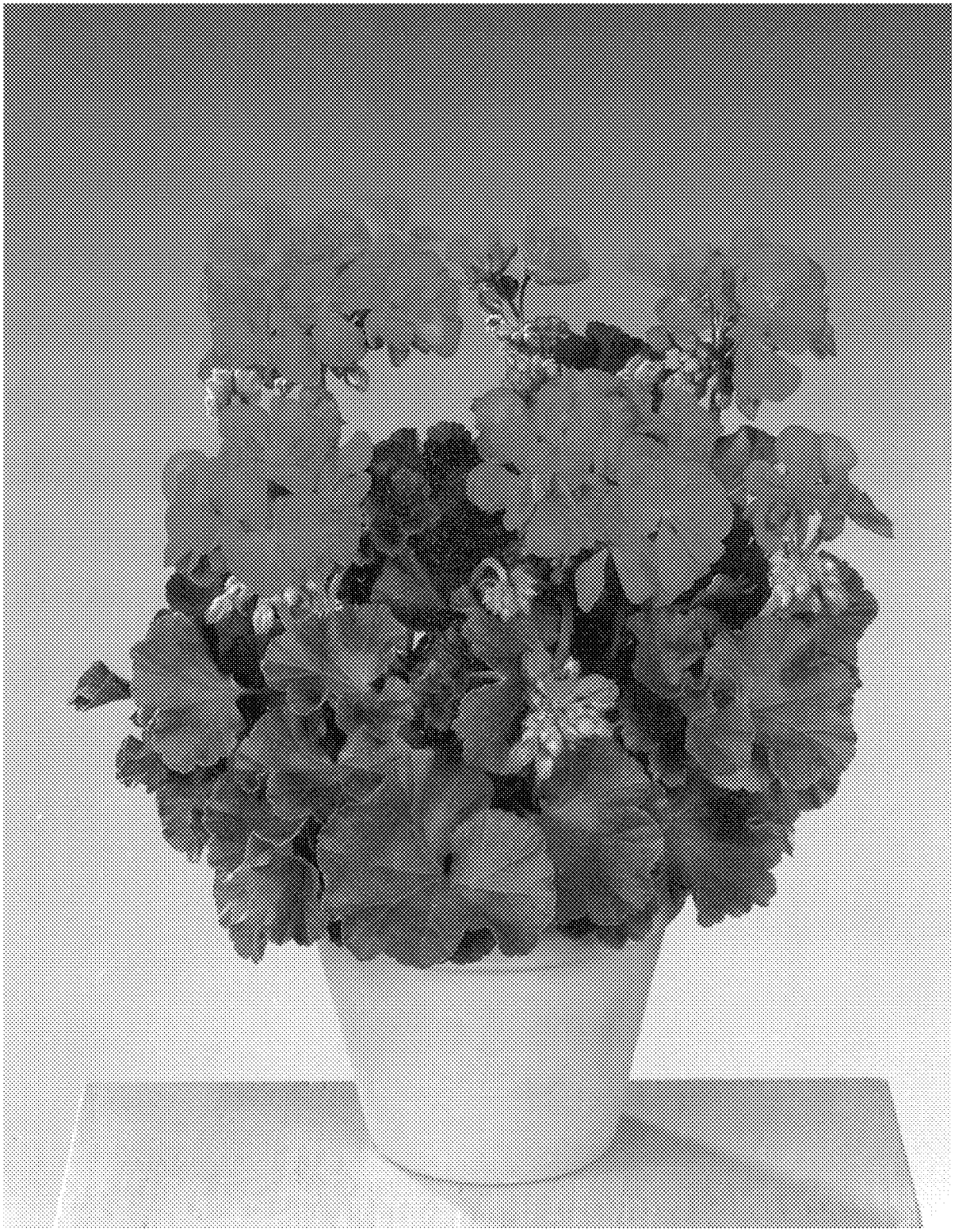

* * * * *